US011628245B2

(12) United States Patent
Dijkstra et al.

(10) Patent No.: US 11,628,245 B2
(45) Date of Patent: Apr. 18, 2023

(54) SKIN TREATMENT DEVICE FOR BALANCING PH VALUE OF SKIN

(71) Applicant: LIGHT TREE, Amstelveen (NL)

(72) Inventors: Alain Dijkstra, Amstelveen (NL); Yvonne Johanna Margaretha Houthuijs, Amstelveen (NL)

(*) Notice: Subject to any disclaimer, the term of this patent is extended or adjusted under 35 U.S.C. 154(b) by 924 days.

(21) Appl. No.: 16/377,234

(22) Filed: Apr. 7, 2019

(65) Prior Publication Data

US 2020/0316270 A1   Oct. 8, 2020

(51) Int. Cl.
| | |
|---|---|
| *A61M 3/02* | (2006.01) |
| *A61M 11/00* | (2006.01) |
| *A61M 35/00* | (2006.01) |
| *A61N 1/04* | (2006.01) |
| *A61Q 19/00* | (2006.01) |
| *A61B 90/80* | (2016.01) |
| *A61B 17/00* | (2006.01) |

(52) U.S. Cl.
CPC .......... *A61M 3/0258* (2013.01); *A61M 11/00* (2013.01); *A61M 35/30* (2019.05); *A61N 1/0428* (2013.01); *A45D 2200/057* (2013.01); *A45D 2200/1054* (2013.01); *A61B 90/80* (2016.02); *A61B 2017/00747* (2013.01); *A61B 2218/001* (2013.01); *A61M 3/0202* (2021.05); *A61M 3/0245* (2013.01); *A61Q 19/00* (2013.01)

(58) Field of Classification Search
CPC ...... A61M 1/774; A61M 35/30; A61M 11/00; A61M 11/044; A61M 35/00; A61M 35/003; A61M 1/71; A61N 1/0428; A61B 90/80; A61B 2017/00747; A61B 2218/001; A45D 2200/057; A45D 2200/1054; A61Q 19/00

See application file for complete search history.

(56) References Cited

U.S. PATENT DOCUMENTS

| 6,471,712 B2 | 10/2002 | Burres | |
|---|---|---|---|
| 7,354,423 B2 | 4/2008 | Zelickson et al. | |
| 2004/0060815 A1* | 4/2004 | Buckley | C02F 1/4618 204/230.2 |
| 2009/0177171 A1* | 7/2009 | Ignon | A61B 17/54 604/289 |
| 2010/0030132 A1* | 2/2010 | Niezgoda | A61M 1/95 604/289 |

(Continued)

FOREIGN PATENT DOCUMENTS

| DE | 102007047618 A1 * | 4/2009 | ........... A45D 34/041 |
|---|---|---|---|
| JP | H10174971 | * 6/1998 | |

*Primary Examiner* — Susan S Su
*Assistant Examiner* — Ted Yang
(74) *Attorney, Agent, or Firm* — Willie Jacques; Emanus, LLC (57) ABSTRACT

A skin treatment device and a method to cleanse and balance pH value of skin. The skin treatment device includes a nozzle to be directed into contact with the skin of a subject. A vacuum pump may be operably coupled to the nozzle for generating a suction force of the nozzle to evacuate impurities from the skin. A liquid replenishing assembly may be operably coupled to the nozzle for atomizing liquid at a pre-defined pH value. The liquid from the liquid replenishing assembly may pass into the nozzle based on the pre-defined pH value. The first control valve may be connected to an outlet of the vacuum pump and an outlet of the liquid replenishing assembly for communication with the nozzle.

13 Claims, 5 Drawing Sheets

(56) References Cited

U.S. PATENT DOCUMENTS

| | | | |
|---|---|---|---|
| 2011/0133001 A1* | 6/2011 | Cooper | B05B 7/066 239/418 |
| 2011/0213319 A1* | 9/2011 | Blott | A61M 27/00 604/291 |
| 2013/0018333 A1* | 1/2013 | Thomason | A61M 35/003 514/762 |
| 2013/0079732 A1* | 3/2013 | Burt | B05B 7/0012 604/290 |
| 2014/0077000 A1* | 3/2014 | Cooper | A61M 35/25 239/302 |
| 2014/0163456 A1* | 6/2014 | Kiss | A61M 37/00 604/24 |
| 2018/0169308 A1* | 6/2018 | Hu | A61M 1/0011 |

* cited by examiner

SKIN TREATMENT DEVICE FOR BALANCING PH VALUE OF SKIN

FIELD OF THE DISCLOSURE

Various embodiments of the present disclosure relate to a skin treatment device. More specifically, various embodiments of the disclosure relate to a skin treatment device and method to cleanse and balance a pH value of skin of a subject.

BACKGROUND

Skin cleansing devices are used to treat the skin of a person by removal of impurities, such as dirt, oil, makeup residue, and sweat. Different types of skin cleansing devices are available in the market. An essential step for healthy and sensitive skin is a balance of pH value of the skin of a user. The pH value represents the hydrogen ratio of the skin that may be calculated on a scale of 1 to 14, with 1 pH value considered as the most acidic and 14 pH value considered as the most alkaline. Generally, the ideal pH value of human skin is 5.5 that is slightly acidic. A balanced pH value may allow the skin of the person to combat germs, exterior aggressors and oil section of the pores of the skin. An imbalanced pH value of the skin may result in various skin problems, such as irritations, redness, pimples and even dermatitis.

In certain scenarios, the skin cleansing devices may be used for removal of dirt on a surface of a facial skin of the person. In some scenarios, the skin cleansing device may be used for removal of deep waste, such as aged keratin and blackheads from the facial skin of the person. It may be difficult for the conventional skin cleansing devices to treat the skin that has imbalanced pH value, thereby resulting in an unsatisfactory cosmetic effect on the skin of the person.

In the U.S. Pat. No. 735,442, 3B2 Brian D. Zelickson et. al discloses a system and method for rejuvenating skin through ablation using a handheld device having a removable treatment component with an abrasive material on one surface of the component which surface is on a portion of the treatment component configured to conform to a skin surface.

In another U.S. Pat. No. 6,471,712B2 Steven A. Burres discloses a Methods and apparatus for abrading, cleaning, massaging, buffing or otherwise treating the skin, fingernails, toenails or other body surfaces. The basic apparatus comprises a small motor mounted within a hand-held housing and a cylindrical member rotatably mounted on the housing. The cylindrical member may be placed in contact with the skin, nails or other body surface while rotating, thereby abrading, cleaning, massaging, buffing or otherwise treating the skin, nails or other body surface. In another embodiment, the device may incorporate a suction apparatus for suctioning away severed particles of skin or other matter.

In above discussed prior arts none of the prior arts are using a balanced pH liquid for the treatment, in the present disclosure the skin treatment device provides a balanced pH liquid based on the user skin. The balanced pH liquid helps in better removal of dirt, maintaining a user skin pH and cleaning of the user skin.

Further limitations and disadvantages of conventional and traditional approaches will become apparent to one skilled in the art, through comparison of described systems with some aspects of the present disclosure, as set forth in the remainder of the present application and with reference to the drawings.

SUMMARY

In view of the foregoing disadvantages inherent in the prior art and the needs as mentioned above, the general purpose of the present disclosure is to provide a skin treatment device that can overcome the disadvantages of the prior art.

Further, the skin treatment device and method are provided to cleanse and balance pH of the skin of a subject, as shown in, and/or described in connection with, at least one of the figures, as set forth more completely in the claims.

Various aspects of a skin treatment device and a method to cleanse and balance pH value of skin are disclosed. According to an aspect of the present disclosure, the skin treatment device includes a nozzle to be directed into contact with the skin of a subject. A vacuum pump may be operably coupled to the nozzle for generating a suction force of the nozzle to evacuate impurities from the skin. A liquid replenishing assembly may be operably coupled to the nozzle for atomizing liquid at a pre-defined pH value. The liquid from the liquid replenishing assembly may pass into the nozzle based on the pre-defined pH value. The first control valve may be connected to an outlet of the vacuum pump and an outlet of the liquid replenishing assembly for communication with the nozzle.

Hence unlike the prior art, the present disclosure uses liquid at a predefined pH along with the suction mechanism that allows the better cleaning. Further, when the liquid applied to the user skin is according to the user skin pH, it helps the skin to rejuvenate smoothly and quickly.

These and other features and advantages of the present disclosure may be appreciated from a review of the following detailed description of the present disclosure, along with the accompanying figures in which like reference numerals refer to like parts throughout.

DETAILED DESCRIPTION

Certain embodiments of the disclosure may be found in a skin treatment device and method to balance pH value of skin of a subject and to cleanse the skin from impurities. Various embodiments of the disclosure provide a skin treatment device that may include a nozzle to be directed into contact with the skin of a subject. The subject may correspond to a person who needs treatment of the skin. A vacuum pump may be operably coupled to the nozzle for generating a suction force of the nozzle to evacuate impurities from the skin of the subject. Further, a liquid replenishing assembly may be operably coupled to the nozzle for atomizing liquid at a pre-defined pH value. A first control valve may be connected to an outlet of the vacuum pump and an outlet of the liquid replenishing assembly for communication with the nozzle.

Various embodiments of the disclosure provide a skin treatment device to treat the skin of a subject by balancing the pH value of the skin. The balanced pH value of the skin may further result in healthy skin, such as, retaining moisture of the skin, control of body oils that secret from pores of the skin, and treatment of facial inflammation. The balanced pH value of the skin may result in strong immunity of the skin, delayed moisture loss, delayed skin aging and glowing skin. The skin treatment device may cleanse the skin of the subject by removal of impurities from the surface of the skin of the subject. The skin treatment device may be configured to receive a pH value and suction force to be set based on user input, via a user interface (UI) element on a display screen of the skin treatment device that may be easy to use. The skin treatment device may be communicatively coupled to a plurality of mobile applications through a communication network, such as wireless local area network (WLAN), Bluetooth and Zigbee. The skin treatment device may be handheld, self-operating, convenient to carry and flexible to use.

Figure 1A:
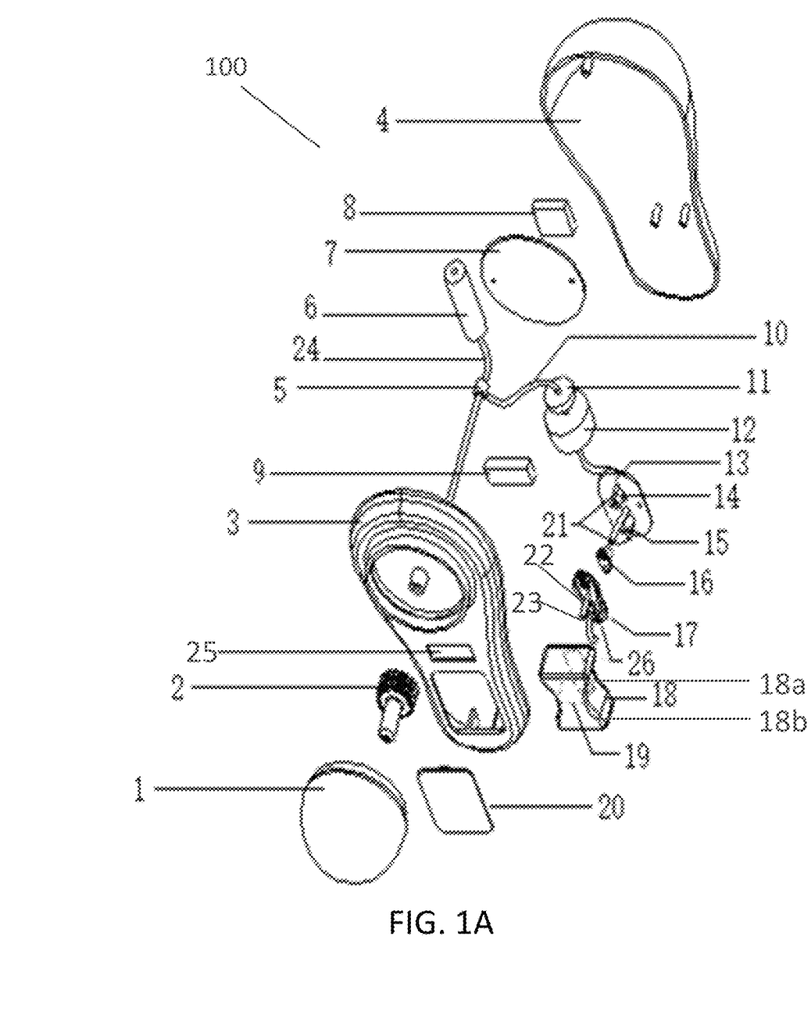
FIG. 1A and FIG. 1B are diagrams that illustrate an exploded view and a cross-sectional view of a skin treatment device respectively, in accordance with a first embodiment of the disclosure.
Figure 1B:
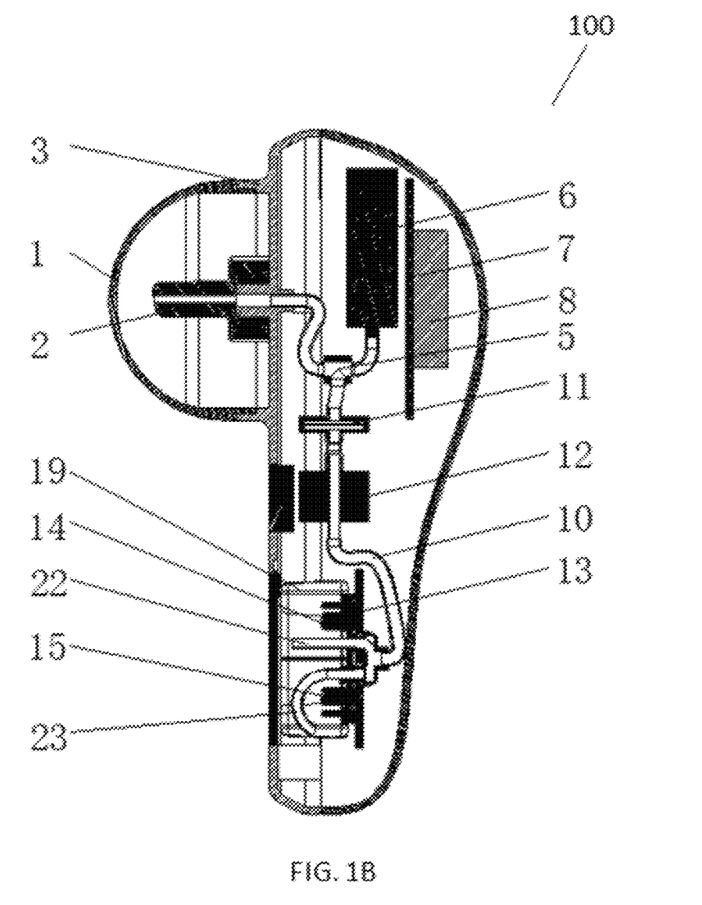

FIG. 1A and FIG. 1B are diagrams that illustrate an exploded view and a cross-sectional view of a skin treatment device respectively, in accordance with an embodiment of the disclosure.

With reference to FIG. 1A and FIG. 1B, there is shown a skin treatment device 100 that may include a plurality of internal structural members, such as, a protective cover 1, a nozzle 2, a front cover 3, a rear cover 4, a first control valve 5, a vacuum pump 6, a control panel 7, a battery 8, a display screen 9, a liquid supply pipe 10, a liquid atomizing sheet 11, a liquid pump 12, an electrode mounting plate 13, a cathode 14, an anode 15, a second control valve 16, a sealant 17, a liquid storage container 18, a first container 18a, a second container 18b, a diaphragm 19, a front cover 20, a plurality of pH sensors 21, such as a pH sensor 21a and a pH sensor 21b (not shown), a first pipe 22, a second pipe 23, a gas pipe 24, a display frame 25, and a plurality of perforated films 26. The skin treatment device may include a liquid replenishing assembly. The liquid replenishing assembly may comprise the liquid storage container 18, the first container 18a, the second container 18b, the first pipe 22, the second pipe 23, the diaphragm 19, an electrolysis liquid device, a hydration system, the second control valve 16. The electrolysis liquid device may comprise of the electrode mounting plate 13, the cathode 14, the anode 15, the pH sensor 21a and the pH sensor 21b. The hydration system may comprise of the liquid supply pipe 10, the liquid atomizing sheet 11, and liquid pump 12.

The skin treatment device 100 may be handled by a user who operates the skin treatment device 100 on the skin of a subject. The subject may correspond to a person who needs treatment of skin, such as cleansing of the skin and balancing of pH value of the skin. Alternatively, the subject may also be the user who operates the skin treatment device 100 on the skin.

The protective cover 1 may be configured to cover the nozzle 2. Further, the protective cover 1 may be configured in two states, i.e., closed state and opened state. In the opened state of the protective cover 1, the skin treatment device 100 may be configured to operate on the skin of the subject. The protective cover 1 may be configured to protect the nozzle 2 of the skin treatment device 100 from any damage.

The nozzle may be configured to suck impurities, such as dirt, oil, makeup residue and sweat from the skin of the subject. Alternatively stated, the nozzle 2 may be configured to be directed into contact with the skin of the subject. The nozzle 2 may be connected to the vacuum pump 6, the liquid pump 12 and the liquid storage container 18. The nozzle 2 may be further configured to be detachable from the skin treatment device 100. The nozzle 2 may be cleaned when the nozzle is detached from the skin treatment device 100.

The front cover 3 and the rear cover 4 may be configured to enclose the internal structural members of the skin treatment device 100 inside the front cover and the rear cover. The front cover 3 and the rear cover 4 may be fixed together to load the internal structural members. The front cover 3 and the rear cover 4 may be composed of high temperature resistant and environmentally friendly materials.

The first control valve 5 may be configured to be connected to an outlet of the vacuum pump 6 and an outlet of the liquid replenishing assembly for communication with the nozzle 2. The first control valve 5 may be configured to control the gas pipe 24 at the outlet of the vacuum pump 6 and the liquid supply pipe 10 at the outlet of the liquid pump 12 to communicate with the nozzle 2. The first control valve 5 may correspond to a three-way electric control valve.

The vacuum pump 6 may be operably coupled to the nozzle 2 for generation of suction force of the nozzle 2 to evacuate impurities from the skin of the subject. In accordance with an embodiment, the vacuum pump 6 may be configured to suck air to wipe off impurities from the skin of the subject. The vacuum pump 6 may be operably coupled to the nozzle 2 via a gas pipe 24. The vacuum pump 6 may be further operably coupled to the nozzle 2 via the first control valve 5. An outlet of the vacuum pump 6 may be connected to the gas pipe 24. The gas pipe 24 may be connected to the nozzle 2 through the first control valve 5. In accordance with an embodiment, the vacuum pump 6 may be of small size, strong, with low noise and good sealing.

The control panel 7 may be operably coupled to the nozzle 2, the vacuum pump 6 and the liquid replenishing assembly. In accordance with an embodiment, the control panel 7 may be electrically connected with the electrode mounting plate 13, the display screen 9, the battery 8, the liquid pump 12, the first control valve 5, and the second control valve 16. The control panel 7 may be further configured to control the pH value of the liquid and the suction force of the vacuum pump 6. The control panel 7 may include but is not limited to, a software control center module. The control panel 7 may be further configured to control the opening and closing state of the first control valve 5, and the second control valve 16. The control panel 7 may be integrated with a variety of features, such as with a Bluetooth module or Wi-Fi module, for connection with software application (e.g., mobile application) that may run on a communication device (e.g. mobile).

The battery 8 may be configured to be powered by the control panel 7. The battery 8 may include, but not limited to, a high polymer battery, a battery with small volume, a battery with large volume, a battery with a high explosion-proof safety factor, and a battery with an external power line charged.

The display screen 9 may be electrically connected to the control panel 7. The display screen 9 may be installed in the display frame 25 of the front cover 3. The pre-defined pH value for the liquid may be set via a user interface (UI)

element on the display screen 9. Further, the operating parameters, such as the suction force of the vacuum pump 6 may be set via the user interface (UI) element on the display screen 9.

The liquid supply pipe 10 may correspond to an outlet pipe of the liquid pump 12. The liquid supply pipe 10 may adopt an environmentally-friendly food grade soft material that may have a strong sealing property, acid resistance, and alkali resistance.

The liquid atomizing sheet 11 may be an essential structural element in the hydration system. The liquid atomizing sheet 11 may be mounted on the outlet of the liquid supply pipe 10 of the liquid pump 12. The liquid atomizing sheet 11 may be configured to atomize the liquid in the liquid storage container 18 and transmits the atomized liquid to the outlet of the nozzle 2. The liquid atomizing sheet 11 may use a micro-ultrasound. The liquid atomizing sheet 11 may have high permeability. The liquid atomizing sheet 11 may be configured to atomize a large volume of liquid.

The liquid pump 12 may be an essential structural element in the hydration system. The liquid pump 12 may be connected to the liquid storage container 18 via an inlet of a liquid supply pipe 10 of the liquid pump 12 and connected to the nozzle 2 via an outlet of the liquid supply pipe 10 of the liquid pump 12. The liquid in the liquid storage container 18 may be passed through the liquid atomizing sheet 11 to reach the skin of the subject. The liquid pump 12 may correspond to a micropump that may be small in size, low in noise and high in sensitivity.

The electrode mounting plate 13 may be a structural element of the electrolysis liquid device. The electrode mounting plate 13 may be configured to mount the cathode 14, the anode 15, the pH sensor 21*a*, and the pH sensor 21*b* on the electrode mounting plate 13.

The cathode 14 may be a structural element of the electrolysis liquid device. The cathode 14 may correspond to a negative electrode of a power source of the electrolysis liquid device. The cathode 14 may extend into the first container 18*a* via one end of the cathode 14. The cathode 14 may be made of yttrium oxide. Further, the cathode 14 may have high electrolysis efficiency.

The anode 15 may be a structural element of the electrolysis liquid device. The anode 15 may correspond to a positive electrode of a power supply of an electrolyzed liquid device. The anode 15 may extend into the second container 18*b* via one end of the anode 15. The anode 15 may be made of cerium oxide. Further, the anode may be an excellent catalyst in an acid-alkaline environment.

The second control valve 16 may be a structural element of the liquid replenishing assembly. The second control valve 16 may have three outlets that are connected to the liquid supply pipe 10, the first pipe 22, and the second pipe 23 respectively. The second control valve 16 may be operably coupled to the first container 18*a* via the first pipe 22, the second container 18*b* via the second pipe 23 and to the liquid supply pipe 10 of the liquid pump 12. The liquid supply pipe 10 of the liquid pump 12 may be operably coupled to the first control valve 5 and the liquid pump 12. The second control valve 16 may be configured to receive control command of the control panel 7 to control the alkaline liquid flow in the first pipe 22 to the first container 18*a*, the acidic liquid flow in the second pipe 23 to the second container 18*b*. The liquid may be supplied to the nozzle 2 from the first container 18*a* and the second container 18*b* via the second control valve 16.

The sealant 17 may be mounted between the liquid storage container 18 and the electrode mounting plate 13 of the liquid storage container 18. The sealant 17 may be configured to seal the liquid storage container 18. The cathode 14, the anode 15, and the pH sensor 21 may penetrate into the liquid storage container 18 when the sealant 17 may be mounted between the liquid storage container 18 and the electrode mounting plate 13. The sealant 17 may be fixed to the liquid storage container 18. The sealant 17 may be configured to be detachable from the liquid storage container 18. The sealant 17 may be cleaned when detachable from the liquid storage container 18. The liquid storage container 18 and the sealant 17 may be taken out together to clean and change the liquid. The sealant 17 may be made up of a food grade soft material and integrally molded.

The liquid storage container 18 may be configured to carry electrolysis of the liquid, such as natural water electrolysis. The liquid storage container 18 may be structurally separated into the first container 18*a* (such as an alkaline water container) and the second container 18*b* (such as, an acidic water container) by the diaphragm 19. In accordance with an embodiment, one end of the cathode 14 may be immersed in the water of the alkaline water container, and one end of the anode 15 may be immersed in the water of the acidic water container. The liquid storage container 18 may be configured to be detachable that aids in easy cleaning of the liquid storage container 18 and changing liquid in the liquid storage container 18. The liquid storage container 18 may be made of a high-temperature resistant food grade material with high hydrolytic stability.

The diaphragm 19 may be located in the liquid storage container 18 to separate the liquid in which the cathode 14 and the anode 15 are located into the first container 18*a* (such as an alkaline water container) and the second container 18*b* (such as, an acidic water container). The diaphragm 19 may correspond to a separator. In accordance with an embodiment, the diaphragm 19 (or separator) may be a chloralkali ion exchange membrane that may have a cation selective permeability to allow only cations and water molecules to pass through, and other ions may be difficult to permeate. The diaphragm 19 can also be made of a highly conductive solid metal sheet that completely separates the liquid storage container 18 into two separate tanks, and liquid may not flow between the first container 18*a* (such as, the alkaline water container) and the second container 18*b* (such as, the acid water container). The diaphragm 19 may be made of a high-temperature resistant food grade material with high hydrolytic stability.

The front cover 20 of the liquid storage container 18 may cover the liquid storage container 18 to facilitate normal watering and pouring of water, in accordance with an embodiment. The front cover 20 may be configured to be opened for the detachment of the liquid storage container 18 to clean and change the liquid in the liquid storage container 18. The front cover 20 may be made of high temperature resistant and environmentally friendly material.

The plurality of sensors, such as the pH sensor 21*a* and the pH sensor 21*b* may be the structural elements of the electrolysis liquid device. The pH sensor 21*a* and the pH sensor 21*b* may be mounted on the electrode mounting plate 13. The pH sensor 21*a* and the pH sensor 21*b* may be located in the first container 18*a* (such as an alkaline water container) and the second container 18*b* (such as an acid water container) respectively for detecting the pH value of the liquid in the liquid storage container 18. The detected pH value of the liquid may be used as data for display, setting, and control by the control panel 7.

The first pipe 22 and the second pipe 23 may be operably coupled with the liquid pump 12 via the second control valve 16. The first pipe 22 may have an inlet inside the first container 18a. The second pipe 23 may have an inlet inside the second container 18b.

The gas pipe 24 may be configured to suck impurities from the skin of the subject. The vacuum pump 6 may be operably coupled to the nozzle 2 for generating a suction force of the nozzle 2 to evacuate impurities from the skin of the subject.

The display frame 25 may be configured to install the display screen 9 inside the display frame 25 for a user to set pH value for treatment of skin and the suction force value to suck impurities from the skin of the subject through a user interface element.

The plurality of perforated films 26 may be provided on the sealant 17. The perforated film 26 may be configured to pass through the cathode 14, the anode 15, and the pH sensor 21a and the pH sensor 21b. The plurality of perforated films 26 may be configured to prevent leakage from the liquid storage container 18. The plurality of perforated films 26 may be made of a soft material and integrally molded.

In operation, the skin treatment device 100 may be brought in contact with the skin of the subject to cleanse the skin and balance the pH value of the skin of the subject. The skin may be of a face, neck or any other body part of the subject. The subject may be a human or an animal. In accordance with an embodiment, the pre-defined pH value may be set via a user interface (UI) element on the display screen 9 of the skin treatment device. The liquid storage container 18 may be filled with the liquid, such as water for electrolysis of the liquid. The operation of the electrolysis is explained in detail in FIG. 2.

In accordance with an embodiment, the control panel 7 may be configured to activate the vacuum pump 6 for evacuation of the impurities from the surface of the skin of the subject. The nozzle 2 may be configured to suck away the impurities, such as dirt, makeup, and sweat from the skin surface of the subject. The control panel 7 may be configured to control the first control valve 5 to connect the nozzle 2 and the liquid supply pipe 10 to start. The electrolyzed liquid device, the liquid pump 12, and the liquid atomizing sheet 11 may atomize the liquid (such as water) to a set pre-defined pH value to balance the pH of the skin of the subject. The atomized liquid (vapors) may be transmitted to an outlet of the nozzle 2 to lubricate the skin and balance the pH of the skin.

Figure 2:
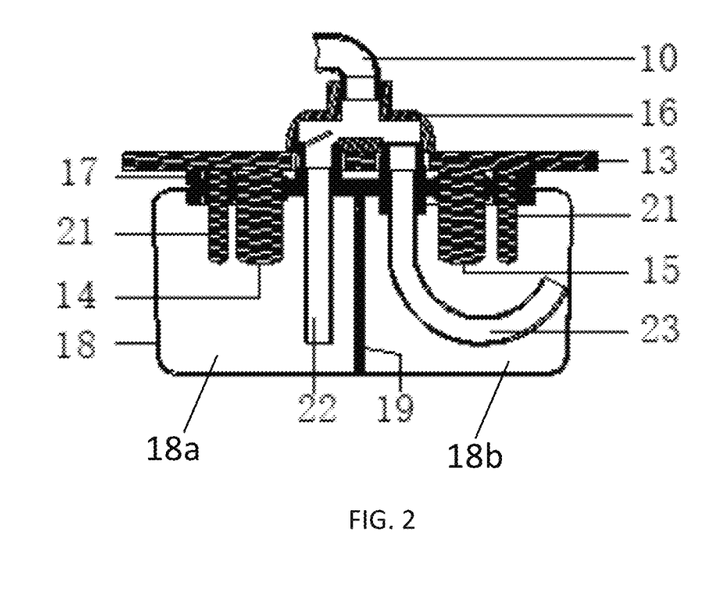
FIG. 2 is a cross-sectional view that illustrates the structure of the electrolysis liquid device of the skin treatment device illustrated in FIG. 1.

FIG. 2 is a cross-sectional view that illustrates the structure of the electrolysis liquid device of FIG. 1.

With reference to FIG. 2, there is shown an electrolysis liquid device of the skin treatment device 100 that shows a plurality of internal structural members interacting with a plurality of the internal structural members of the skin treatment device 100, viz., the liquid supply pipe 10, the electrode mounting plate 13, the cathode 14, the anode 15, the second control valve 16, the sealant 17, the liquid storage container 18, the first container 18a, the second container 18b, the diaphragm 19, the pH sensor 21a, the pH sensor 21b, the first pipe 22, and the second pipe 23.

In accordance with an embodiment, the diaphragm 19 may correspond to a conductive medium. The liquid storage container 18 may be configured to receive a direct current (DC) voltage that may be applied to the liquid (such as, the water). Based on the applied DC voltage, the liquid may be decomposed by the electrodes, such as the cathode 14 and the anode 15 to separate the alkaline liquid and the acidic liquid respectively. In accordance with an embodiment, the liquid may correspond to the water. Since calcium, magnesium, sodium, potassium and other minerals in the water may accumulate in the cathode 14, the hydroxide ions (OH—) may increase to become the alkaline water. The alkaline water may be referred to as reduced water. The reduced water may be suitable for drinking and health care. Oxygen, sulfuric acid, sulfur and the like may be induced to the anode 15, thereby hydrogen ions (H+) may be added to form the acidic water. The acidic water may be referred to as oxidized water. The acidic water may be suitable for cleaning, disinfection, and beauty.

Typically, tap water may be composed of 13-15 small molecular groups because of the action of hydrogen bonds. Under the action of an electric field, the hydrogen bonds of water molecules may be opened, and small molecule water composed of 5-6 water molecules may be generated. Simultaneously, under the action of the electric field, some of the cations, such as $Ca^{2+}$, $Mg^{2+}$, $K+$, $H+$ in the solution may move towards the cathode 14. According to the strength of the obtained electrons, the Hydrogen ions (H+) may undergo a reduction reaction, and the electrons may become hydrogen that may be reduced due to the concentration of Hydrogen ions (H+). The concentration of hydroxide ions may increase and the water body may be weakly alkaline. The pH value may be greater than 7, and the water generated by the cathode 14 may be called alkaline water. Simultaneously, at the anode 15, some of the anions Cl—, $SO_4^{2-}$, $NO_3-$, $NO_2-$, OH— may move towards the anode 15. Among the many anions, the hydroxide ions may be most likely to lose electrons, then an oxidation reaction occurs, and the electrons may be lost to generate oxygen and water. As the concentration of hydroxide ions may decrease, the concentration of H ions may increase. The water body may be weakly acidic, the pH value may be less than 7, and the water generated by the anode 15 may be called as acidic ionized water.

In order to produce different pH waters for output to the nozzle 2, the water may be added to the liquid storage container 18 for electrolysis. The pH value of the liquid storage container 18 may depend on whether the hydrogen ion (H+) concentration is greater or less than the hydroxide ion (OH—) concentration. The pH may be controlled as long as the concentration of H+ and OH— may be controlled byte electrolysis liquid device. In an exemplary embodiment, when pH required is 5.5, the OH— in the acidic water tank (the second container 18b) where the anode 15 may be located is most likely to lose electrons to be oxidized to form water. Therefore, the OH— may be reduced, and the concentration of OH— may be less than the H+ concentration. Consequently, the water may become acidic. The pH sensors 21a and 21b may be configured to detect the values of acidic water and alkaline water in real time while electrolyzing. When the pH of the water reaches 5.5, the electrolysis is stopped, thereby obtaining a set pH value. For example, when pH 9.5 is required, the H+ electron in the alkaline water tank where the cathode 14 is located becomes hydrogen gas, H+ decreases. The concentration of H+ may be less than the OH-concentration, thereby the water becomes alkaline. The pH sensor 21a and 21b may detect the pH value of the water in the chamber in real time. When the pH value may reach 9.5, the electrolysis may stop.

Figure 3:
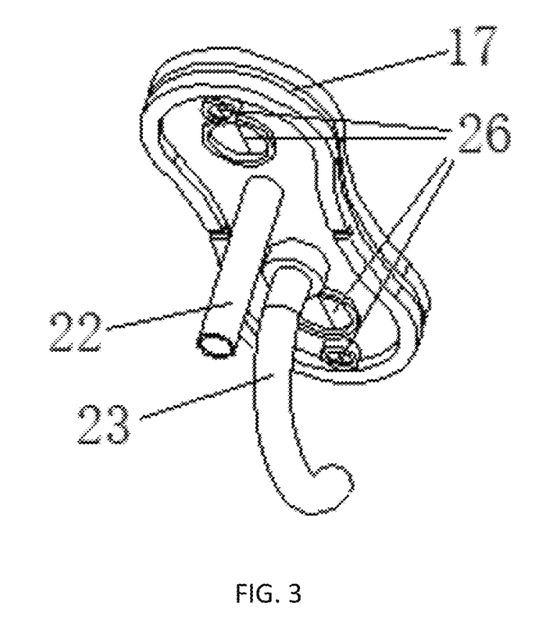
FIG. 3 is a diagram that illustrates a structural view of the sealant of the skin treatment device of FIG. 1, in accordance with an embodiment of the disclosure.

FIG. 3 is a diagram that illustrates a structural view of the sealant 17 of the skin treatment device of FIG. 1, in accordance with an embodiment of the disclosure. FIG. 3 is explained in conjunction with the elements of FIG. 1a, FIG. 1b and FIG. 2.

With reference to FIG. 3, there is shown a sealed cover of the skin treatment device. There may be further shown a plurality of perforated films 26, the first pipe 22 and the second pipe 23. In accordance with an embodiment, the liquid storage container 18 and the sealant 17 may be taken out together to clean and change the liquid. In order to be sealed when installed again, as shown in FIG. 3, the plurality of perforated films 26 may be provided on the sealant 17. The plurality of perforated film 26 may be configured to pass through the cathode 14, the anode 15, and the pH sensors 21a and 21b respectively. The plurality of perforated films 26 and the sealant 17 may be made of a soft material and integrally molded. The intermediate portion of the perforated film 26 may be cut so that when the cathode 14, the anode 15 and the pH sensors 21a and 21b may pass through. The soft material may function as a seal to prevent the liquid storage container 18 from leakage after the liquid storage container 18 may be filled with the water.

Figure 4:
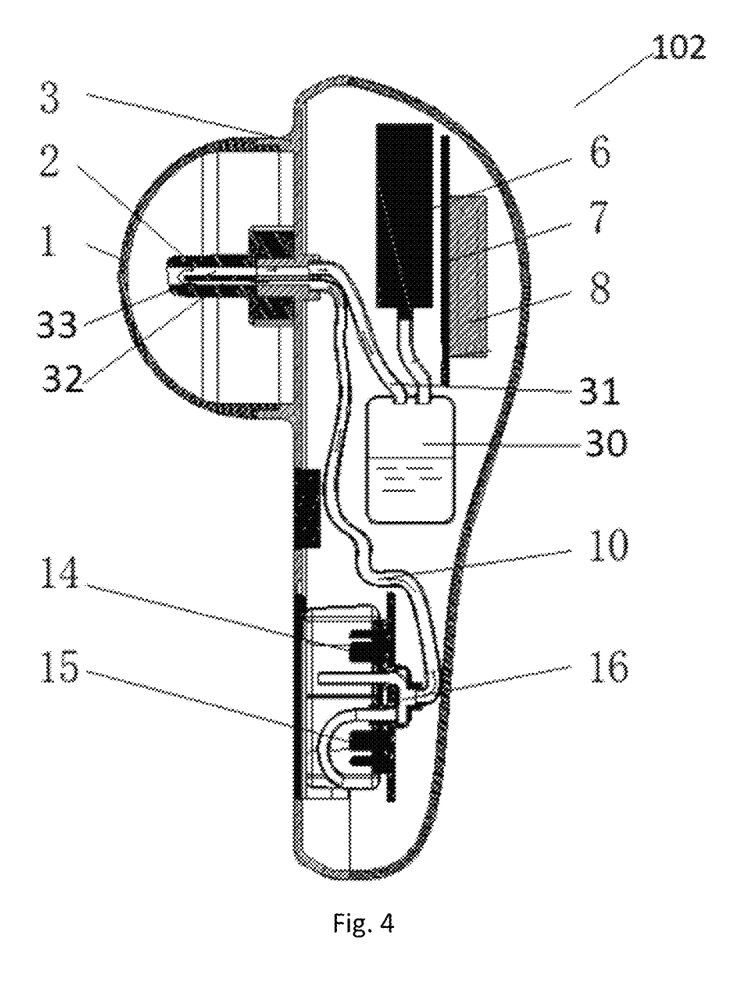
FIG. 4 is a diagram that illustrates a cross-sectional view to show a structure of a skin treatment device, in accordance with a second embodiment of the disclosure.

FIG. 4 is a diagram that illustrates a cross-sectional view to show a structure of a skin treatment device 102, in accordance with a second embodiment of the disclosure. FIG. 4 may be explained in conjunction with elements of the FIG. 1a, FIG. 1b, FIG. 2, and FIG. 3.

With reference to FIG. 4, a skin treatment device 102 may be shown in accordance with a second embodiment. The structural elements may be shown as a protective cover 1, a nozzle 2, a front cover 3, a rear cover 4, a vacuum pump 6, a control panel 7, a battery 8, a liquid supply pipe 10, a cathode 14, an anode 15, a second control valve 16, a sewage container 30, a drainage pipe 31, an inlet passage 32, and a drainage passage 33.

The skin treatment device 102 may differ from the skin treatment device 100 with few structural element changes. For the sake of brevity, structural elements that illustrate the difference from the skin treatment device 100 of FIG. 1a and FIG. 1b may be shown in FIG. 4. With reference to FIG. 4, the second control valve 16, the sewage container 30, the drainage pipes 31, the inlet passage 32, and the drainage passage 33 may be structural elements different from structural elements of the skin treatment device 100 of FIG. 1a and FIG. 1b.

In accordance with an embodiment, the nozzle 2 may be directed into contact with the skin of a subject. The nozzle 2 may include an inlet passage 32 and a drainage passage 33 for liquid that has to be atomized at a pre-defined pH value. The inlet passage 32 and the drainage passage 33 may communicate at an opening of the nozzle 2. In accordance with an embodiment, the passages in the nozzle 2 may be divided into the inlet passage 32 and the drainage passage 33 based on partitions in the nozzle 2. The inlet passage 32 may communicate with the liquid supply pipe 10. The drainage passage 33 may communicate with the drainage pipe 31.

The vacuum pump 6 may be operably coupled to the nozzle 2 for generation of suction force of the nozzle to evacuate impurities from the skin of the subject. The electrolysis liquid device for yielding the liquid at the pre-defined pH value. The sewage container 30 may be operably coupled to the nozzle 2, the vacuum pump 6 and the electrolysis liquid device. The sewage container 30 may be sealed and in communication with an outlet of the vacuum pump 6. The drainage passage 33 may be connected to the sewage container 30.

In the present embodiment, the suction pump is not provided, and after the vacuum pump 6 is evacuated, a vacuum may be formed on the surface of the skin near the nozzle 2, and in the liquid storage container 18. Consequently, the water may flow along the liquid supply pipe 10.

The inlet passage 32, the drainage passage 33, and the drainage passage 33 may flow into the sewage container 30. Therefore, the skin treatment device 102 may be configured to replenish the skin of the subject with acidic or alkaline liquid (such as alkaline water or acidic water) based on the cleansing of the skin of the subject.

In other embodiments, the acidic water and the alkaline water may be prepared in advance and injected into an acidic water container and an alkaline water container respectively. Acidic or alkaline water may be added directly to the alkaline water container in the acidic water container and an alkaline water container. Chemical raw materials may directly change the pH of the water, however high precision in pH adjustment operation may be required with manual intervention.

Various embodiments of the present disclosure may be found in a method and a skin treatment device (e.g., the skin treatment device 100) that cleanses the skin of a subject and balances pH value of the skin of the subject. The skin treatment device may include a nozzle, a vacuum pump, a liquid replenishing assembly, and a first control valve. The skin treatment device may include a nozzle to be directed into contact with the skin of a subject. The skin treatment device may include a vacuum pump operably coupled to the nozzle for generating a suction force of the nozzle to evacuate impurities from the skin of the subject. The skin treatment device may include a liquid replenishing assembly operably coupled to the nozzle for atomizing liquid at a pre-defined pH value. The liquid from the liquid replenishing assembly passes into the nozzle based on the pre-defined pH value. The skin treatment device may include a first control valve connected to an outlet of the vacuum pump and an outlet of the liquid replenishing assembly for communication with the nozzle.

In accordance with an embodiment, the skin treatment device may further comprise a control panel operably coupled to the nozzle, the vacuum pump, and the liquid replenishing assembly. The control panel may further be configured to control the pH value of the liquid and the suction force of the vacuum pump.

In accordance with an embodiment, the vacuum pump may be operably coupled to the nozzle via a gas pipe. The vacuum pump may be further operably coupled to the nozzle via the first control valve.

In accordance with an embodiment, the liquid replenishing assembly may further comprise a liquid storage container separated into at least a first container and a second container via a diaphragm. The first container may correspond to an alkaline liquid container and the second container may correspond to an acidic liquid container.

In accordance with an embodiment, the liquid replenishing assembly may further comprise an electrolysis liquid device for yielding the liquid in the liquid storage container at the pre-defined pH value.

In accordance with an embodiment, the electrolysis liquid device may further comprise an electrode mounting plate, an anode, and a cathode. The anode may be mounted on the electrode mounting plate. The anode may extend into the second container via one end of the anode. The cathode may be mounted on the electrode mounting plate. The cathode may extend into the first container via one end of the cathode.

In accordance with an embodiment, the electrolysis liquid device may further comprise a plurality of pH sensors mounted on the electrode mounting plate. The plurality of pH sensors may extend into the liquid storage container. The plurality of pH sensors may be further configured to detect the pH value of the liquid in the liquid storage container.

In accordance with an embodiment, the liquid replenishing assembly may further comprise a hydration system for balancing the pH value of the skin of the subject brought in contact with the nozzle.

In accordance with an embodiment, the hydration system may further comprise a liquid pump connected to the liquid storage container via an inlet of a liquid pipe of the liquid pump and connected to the nozzle via an outlet of the liquid pipe of the liquid pump.

In accordance with an embodiment, the hydration system may further comprise a liquid atomizing sheet mounted on the outlet of the liquid pipe of the liquid pump.

In accordance with an embodiment, the liquid replenishing assembly may further comprise a second control valve operably coupled to the first container via a first pipe, the second container via a second pipe and to the outlet pipe of the liquid pump. The liquid pipe of the liquid pump may be operably coupled to the first control valve and the liquid pump.

In accordance with an embodiment, the liquid storage container may further comprise a liquid seal cover. The sealant may be mounted between the liquid storage container and the electrode mounting plate of the liquid storage container.

In accordance with an embodiment, the sealant may further comprise a plurality of perforated films. The plurality of perforated films may be configured to prevent leakage from the liquid storage container.

In accordance with an embodiment, the liquid storage container may be further configured to be detachable from the skin treatment device based on a position of a cover attached to the liquid storage container.

In accordance with an embodiment, the skin treatment device may further comprise a display screen. The pre-defined pH value may be set via a user interface (UI) element on the display screen.

In accordance with an embodiment, the nozzle may be further configured to be detachable from the skin treatment device.

In accordance with an embodiment, a skin treatment device may comprise a nozzle to be directed into contact with the skin of a subject. The nozzle may comprise an inlet passage and a drainage passage for liquid to be atomized at a pre-defined pH value. The inlet passage and the drainage passage may communicate at an opening of the nozzle. A vacuum pump may be operably coupled to the nozzle for generating the suction force of the nozzle to evacuate impurities from the skin of the subject. An electrolysis liquid device for yielding the liquid at the pre-defined pH value. A sewage container may be operably coupled to the nozzle, the vacuum pump, and the electrolysis liquid device.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments that fall within the scope of the appended claims.

What is claimed is:

1. A skin treatment device, comprising:
a nozzle to be directed into contact with skin of a subject;
a vacuum pump operably coupled to the nozzle for generating a suction force of the nozzle to evacuate impurities from the skin of the subject;
a liquid replenishing assembly operably coupled to the nozzle for atomizing a liquid provided in the liquid replenishing assembly at a pre-defined pH value, wherein the liquid from the liquid replenishing assembly passes into the nozzle at the predefined pH value; and
a first control valve connected to an outlet of the vacuum pump and an outlet of the liquid replenishing assembly for communication with the nozzle,
wherein the liquid replenishing assembly further comprises a hydration system for balancing the pH value of the skin of the subject brought in contact with the nozzle;
wherein the hydration system further comprises a liquid pump connected to a liquid storage container via an inlet of a liquid pipe of the liquid pump and connected to the nozzle via an outlet of the liquid pipe of the liquid pump;
wherein the hydration system further comprises a liquid atomizing sheet mounted on the outlet of the liquid pipe of the liquid pump, the liquid atomizing sheet being configured to atomize the liquid in the liquid storage container and transmit the atomized liquid to the outlet of the nozzle.

2. The skin treatment device according to claim 1, further comprising a control panel operably coupled to the nozzle, the vacuum pump, and the liquid replenishing assembly, wherein the control panel is further configured to control the pH value of the liquid and the suction force of the vacuum pump.

3. The skin treatment device according to claim 1, wherein the vacuum pump is operably coupled to the nozzle via a gas pipe, wherein the vacuum pump is further operably coupled to the nozzle via the first control valve.

4. The skin treatment device according to claim 1, wherein the liquid replenishing assembly further comprises a liquid storage container separated into at least a first container and a second container via a diaphragm, wherein the first container corresponds to an alkaline liquid container and the second container corresponds to an acidic liquid container.

5. The skin treatment device according to claim 4, wherein the liquid replenishing assembly further comprises an electrolysis liquid device for yielding the liquid in the liquid storage container at the pre-defined pH value.

6. The skin treatment device according to claim 5, wherein the electrolysis liquid device further comprises:
an electrode mounting plate;
an anode mounted on the electrode mounting plate, wherein the anode extends into the second container via one end of the anode; and
a cathode mounted on the electrode mounting plate, wherein the cathode extends into the first container via one end of the cathode.

7. The skin treatment device according to claim 6, wherein the electrolysis liquid device further comprises a plurality of pH sensors mounted on the electrode mounting plate, wherein the plurality of pH sensors extends into the liquid storage container and wherein the plurality of pH sensors is further configured to detect the pH value of the liquid in the liquid storage container.

8. The skin treatment device according to claim 4, wherein the liquid replenishing assembly further comprises a second control valve operably coupled to the first container via a first pipe, the second container via a second pipe and to an outlet pipe of the liquid pump, wherein the liquid pipe of the liquid pump is operably coupled to the first control valve and the liquid pump.

9. The skin treatment device according to claim 4, wherein the liquid storage container further comprises a liquid seal cover, wherein a sealant is mounted between the liquid storage container and an electrode mounting plate of the liquid storage container.

10. The skin treatment device according to claim 9, wherein the sealant further comprises a plurality of perforated films, wherein the plurality of perforated films are configured to prevent leakage from the liquid storage container.

11. The skin treatment device according to claim 9, wherein the liquid storage container is further configured to be detachable from the skin treatment device based on a position of a cover attached to the liquid storage container.

12. The skin treatment device according to claim 1, further comprising a display screen, wherein the pre-defined pH value is set via a user interface (UI) element on the display screen.

13. The skin treatment device according to claim 1, wherein the nozzle is further configured to be detachable from the skin treatment device.

\* \* \* \* \*